United States Patent
Heer et al.

(10) Patent No.: US 7,560,476 B2
(45) Date of Patent: Jul. 14, 2009

(54) MICROBICIDAL COMPOSITION

(75) Inventors: Beat Heer, Grabs (CH); Gerhard Tiedtke, Gams (CH); Eileen Fleck Warwick, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 849 days.

(21) Appl. No.: 10/803,237

(22) Filed: Mar. 18, 2004

(65) Prior Publication Data

US 2004/0198785 A1    Oct. 7, 2004

Related U.S. Application Data

(60) Provisional application No. 60/458,203, filed on Mar. 26, 2003.

(51) Int. Cl.
*A61K 31/425* (2006.01)
*A01N 43/80* (2006.01)
(52) U.S. Cl. ..................................... 514/372
(58) Field of Classification Search ................ 424/406; 514/372
See application file for complete search history.

(56) References Cited

U.S. PATENT DOCUMENTS 4,295,887 A * 10/1981 Buckley et al. .......... 106/18.33
6,361,788 B1 * 3/2002 Antoni-Zimmermann et al. ........................ 424/406

FOREIGN PATENT DOCUMENTS

GB        2 208 474        4/1989
JP        2001302418       10/2001

OTHER PUBLICATIONS

Zhang, et al., "Study on mildewcidal ability of latex coatings for building materials", Tuliao Gongye, vol. 31:12-14 (2001) (Abstract only).

* cited by examiner

*Primary Examiner*—Alton N Pryor
(74) *Attorney, Agent, or Firm*—Kenneth Crimaldi

(57) ABSTRACT

A microbicidal composition containing: (a) at least one non-halogenated 2-alkyl-4-isothiazolin-3-one selected from substituted and unsubstituted 2-($C_1$-$C_4$)alkyl-4-isothiazolin-3-ones; and (b) at least one of 2,2'-dithiobis(N-methylbenzamide) and 2-methylbenzisothiazolone.

4 Claims, No Drawings

MICROBICIDAL COMPOSITION

CROSS REFERENCE TO RELATED PATENT APPLICATIONS

This is a non-provisional application of prior pending U.S. provisional application Ser. No. 60/458,203, filed Mar. 26, 2003.

This invention relates to a combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides. Combinations of different microbicides are sometimes used to provide overall control of microorganisms in a particular end use environment. For example, a combination of 2-methylisothiazolin-3-one and 1,2-benzisothiazolin-3-one is disclosed in U.S. Pat. No. 6,361,788. However, there is a need for additional combinations of microbicides having enhanced activity against various strains of microorganisms to provide effective control of the microorganisms that is both quick and long lasting. The problem addressed by this invention is to provide such additional combinations of microbicides.

STATEMENT OF THE INVENTION

The present invention is directed to a microbicidal composition comprising: (a) at least one non-halogenated 2-alkyl-4-isothiazolin-3-one selected from substituted and unsubstituted 2-($C_1$-$C_4$)alkyl-4-isothiazolin-3-ones; and (b) at least one of 2,2'-dithiobis(N-methylbenzamide) and 2-methylbenzisothiazolone.

In one embodiment, the present invention is directed to a paint composition comprising from 50 ppm to 500 ppm of a synergistic microbicide composition. The synergistic microbicide composition comprises: (a) 2-methyl-4-isothiazolin-3-one; and (b) a second microbicide comprising at least one of 2,2'-dithiobis(N-methylbenzamide) and 2-methylbenzisothiazolone. A weight ratio of 2-methyl-4-isothiazolin-3-one to the second microbicide is from 375:1 to 1:6.

DETAILED DESCRIPTION OF THE INVENTION

"DTBMA" is 2,2'-dithiobis(N-methylbenzamide), which has the following structure

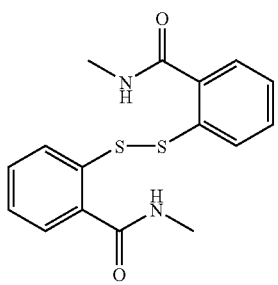

"MBI" is 2-methylbenzisothiazolone, which has the following structure

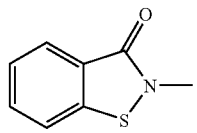

"MI" is 2-methyl-4-isothiazolin-3-one, also referred to by the name 2-methyl-3-isothiazolone.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages (%) are by weight. "Salt-free" means that the composition contains zero or up to 0.5%, preferably zero or up to 0.1%, and more preferably zero or up to 0.01%, of metal salt, based on weight of the composition.

The compositions of the present invention unexpectedly have been found to provide enhanced microbicidal efficacy at a combined active ingredient level lower than that of the individual microbicides. The microbicidal compositions of the present invention are substantially free of halogenated 3-isothiazolone; that is, zero or up to 3%, preferably zero or up to 1% and more preferably zero or up to 0.5%, of halogenated 3-isothiazolone may be present, based on combined weight of halogenated 3-isothiazolone and 2-methyl-3-isothiazolone. Microbicidal compositions dependent on the presence of halogenated 3-isothiazolone are susceptible to chemical degradation and may require additional stabilizer components, such as the aforementioned metal salt stabilizers; salt stabilizers sometimes create unacceptable properties in finished formulations. For this reason it is desirable to provide microbicide formulations substantially free of halogenated 3-isothiazolone, but that still provide the degree of antimicrobial protection provided by the halogenated 3-isothiazolones; such are the microbicidal compositions of the present invention that are based on 2-methyl-3-isothiazolone, which do not require metal stabilizers.

The first microbicide in the composition of this invention comprises at least one non-halogenated 2-alkyl-4-isothiazolin-3-one. The first microbicide is combined with a second microbicide comprising at least one compound chosen from the group consisting of 2,2'-dithiobis(N-methylbenzamide) and 2-methylbenzisothiazolone. The at least one non-halogenated 2-alkyl-4-isothiazolin-3-one is selected from the group consisting of the substituted and unsubstituted 2-($C_1$-$C_4$) alkyl-4-isothiazolin-3-ones, preferably the unsubstituted 2-($C_1$-$C_4$)alkyl-4-isothiazolin-3-ones, and most preferably 2-methyl-4-isothiazolin-3-one. Substituted 2-($C_1$-$C_4$)alkyl-4-isothiazolin-3-ones may contain ($C_1$-$C_4$)alkyl groups at one or both of the 4- and 5-positions of the isothiazolone ring.

Preferably, a weight ratio of the first microbicide to the second microbicide, i.e., at least one of 2,2'-dithiobis(N-methylbenzamide) and 2-methylbenzisothiazolone, is from 750:1 to 1:20, more preferably from 375:1 to 1:20, and most preferably from 100:1 to 1:6. When the second microbicide is 2-methylbenzisothiazolone, the weight ratio preferably is from 750:1 to 1:6, more preferably from 125:1 to 1:6. When the second microbicide is 2,2'-dithiobis(N-methylbenzamide), the weight ratio preferably is from 375:1 to 1:20, more preferably from 100:1 to 1:20.

The first microbicide may be used in the synergistic mixtures of the present invention "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials and charcoal. It is preferred that the first microbicide is formulated in water.

When a second microbicide component having low water solubility is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A second microbicide component having low water solubility also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, stabilizers, scale inhibitors and anti-corrosion additives.

Any formulation of the first microbicide may be used with any formulation of the second microbicide component in the synergistic mixtures of the present invention. When both the first microbicide and the second microbicide component are each first formulated with a solvent, the solvent used for the first microbicide may be the same as or different from the solvent used to formulate the other commercial microbicide. It is preferred that the two solvents are miscible. In the alternative, the first microbicide and the other microbicide may be combined directly and then a solvent added to the mixture.

Those skilled in the art will recognize that the first microbicide and the second microbicide component of the present invention may be added to a locus sequentially, simultaneously, or may be combined before being added to the locus. It is preferred that the first microbicide and the second microbicide component be added to a locus simultaneously or combined prior to being added to the locus. When the microbicides are combined prior to being added to a locus, such combination may optionally contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, stabilizers, scale inhibitors and anti-corrosion additives.

The microbicidal compositions of the present invention can be used to inhibit the growth of microorganisms by introducing a microbicidally effective amount of the compositions onto, into, or at a locus subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the microbicidal compositions of the present invention are used to inhibit the growth of microorganisms at a locus selected from one or more of emulsions, dispersions, paints, latexes, household products, cosmetics, toiletries, shampoos, soaps, detergents and industrial cleaners. In particular, the microbicidal compositions are useful in emulsions, dispersions, paints and latexes.

When the synergistic compositions of the present invention are used in personal care compositions, the formulated compositions may also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

The specific amount of the synergistic combinations necessary to inhibit or control the growth of microorganisms in a locus depends upon the particular compounds in the combination and particular locus to be protected. Typically, the amount of the synergistic combinations of the present invention to control the growth of microorganisms in a locus is sufficient if it provides from 0.1 to 10,000 ppm active ingredient of the synergistic mixture in the locus. It is preferred that the synergistic mixture be present in the locus in an amount of at least 0.5 ppm, more preferably at least 1 ppm, more preferably at least 10 ppm and most preferably at least 50 ppm. It is preferred that the synergistic mixture be present in the locus in an amount of no more than 5000 ppm, more preferably no more than 3000 ppm, more preferably no more than 1000 ppm, and most preferably no more than 500 ppm.

EXAMPLES

The synergism of the combinations of the present invention was demonstrated by testing a wide range of concentrations and ratios of the compounds.

Synergism was determined by an industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index ("SI")}$$

wherein:

$Q_A$=concentration of compound A (first component) in ppm, acting alone, which produced an end point (MIC of Compound A).

$Q_a$=concentration of compound A in ppm, in the mixture, which produced an end point.

$Q_B$=concentration of compound B (second component) in ppm, acting alone, which produced an end point (MIC of Compound B).

$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of MI. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient. The synergy of the combinations of the present invention was determined against two bacteria, *Staphylococcus aureus* (*S. aureus*—ATCC #6538) or *Pseudomonas aeruginosa* (*P. aeruginosa*—ATCC #15442), a yeast, *Candida albicans* (*C. albicans*—ATCC 10231), and a mold, *Aspergillus niger* (*A. niger*—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the microbicide combinations of the present invention are shown below in the Tables. In each test, First Component (A) was MI and the Second Component (B) was either DTBMA or MBI. "NG" means that no growth was observed. Each table shows the specific combinations of MI and the second component; results against the microorganisms tested with incubation times; the end-point activity in ppm measured by the MIC for MI alone ($Q_A$), for the second component alone ($Q_B$), for MI in the mixture ($Q_a$) and for second component in the mixture ($Q_b$); the calculated SI value; and the range of synergistic ratios for each combination tested (MI/second component or A/B).

results for DTBMA

| vs. *P. aeruginosa* 9027 in M9GY @ 72 hours | | | vs. *S. aureus* 6538 in M9GY @ 24 hours | | |
|---|---|---|---|---|---|
| $Q_{MI}$ | $Q_{DTBMA}$ | SI | $Q_{MI}$ | $Q_{DTBMA}$ | |
| 25 | 1000 | | 60 | 40 | |
| $Q_{mi}$ | $Q_{dtbma}$ | | $Q_{mi}$ | $Q_{dtbma}$ | SI |
| 5 | 1000 | 1.20 | 10 | 5 | 0.29 |
| 10 | 800 | 1.20 | 15 | 4 | 0.35 |
| 15 | 300 | 0.90 | 20 | 3 | 0.41 |
| 20 | 60 | 0.86 | 25 | 2 | 0.47 |
| 25 | NG | | 30 | 2 | 0.55 |
| | | | 35 | 2 | 0.63 |
| | | | 40 | 2 | 0.72 |
| | | | 45 | 0.8 | 0.77 |
| | | | 50 | 0.4 | 0.84 |
| | | | 60 | NG | |

| vs. *C. albicans* 10231 in PDB @ 48 hours | | | vs. *A. niger* 16404 in PDB @ 72 hours | | |
|---|---|---|---|---|---|
| $Q_{MI}$ | $Q_{DTBMA}$ | SI | $Q_{MI}$ | $Q_{DTBMA}$ | |
| 175 | 40 | | 400 | 1500 | |
| $Q_{mi}$ | $Q_{dtbma}$ | | $Q_{mi}$ | $Q_{dtbma}$ | SI |
| 50 | 2 | 0.34 | 100 | 100 | 0.45 |
| 75 | 2 | 0.48 | 150 | 80 | 0.54 |
| 100 | 1 | 0.60 | 200 | 8 | 0.52 |
| 125 | 0.8 | 0.73 | 250 | 3 | 0.63 |
| 150 | 0.4 | 0.87 | 300 | 3 | 0.76 |
| 175 | NG | | 400 | NG | |

Results for MBI

| vs. *P. aeruginosa* 9027 in M9GY @ 72 hours | | | vs. *S. aureus* 6538 in M9GY @ 24 hours | | |
|---|---|---|---|---|---|
| $Q_{MI}$ | $Q_{MBI}$ | SI | $Q_{MI}$ | $Q_{MBI}$ | |
| 25 | 200 | | 60 | 8 | |
| $Q_{mi}$ | $Q_{mbi}$ | | $Q_{mi}$ | $Q_{mbi}$ | SI |
| 5 | 200 | 1.20 | 10 | 4 | 0.67 |
| 10 | 60 | 0.70 | 15 | 3 | 0.63 |
| 15 | 30 | 0.75 | 20 | 4 | 0.83 |
| 20 | 20 | 0.81 | 25 | 3 | 0.79 |
| 25 | NG | | 30 | 2 | 0.75 |
| | | | 35 | 2 | 0.83 |
| | | | 40 | 2 | 0.92 |
| | | | 45 | 0.8 | 0.85 |
| | | | 50 | 0.4 | 0.88 |
| | | | 60 | NG | |

| vs. *C. albicans* 10231 in PDB @ 48 hours | | | vs. *A. niger* 16404 in PDB @ 72 hours | | |
|---|---|---|---|---|---|
| $Q_{MI}$ | $Q_{MBI}$ | SI | $Q_{MI}$ | $Q_{MBI}$ | |
| 175 | 8 | | 400 | 60 | |
| $Q_{mi}$ | $Q_{mbi}$ | | $Q_{mi}$ | $Q_{mbi}$ | SI |
| 50 | 1 | 0.41 | 100 | 10 | 0.42 |
| 75 | 0.8 | 0.53 | 150 | 8 | 0.51 |
| 100 | 0.8 | 0.67 | 200 | 4 | 0.57 |
| 125 | 0.4 | 0.76 | 250 | 2 | 0.66 |
| 150 | 0.2 | 0.88 | 300 | 2 | 0.78 |
| 175 | NG | | 400 | NG | |

The results for DTBMA demonstrate synergy at least for ratios of MI:DTBMA ranging from 1:20 (15 ppm MI:300 ppm DTBMA vs. *P. aeruginosa*) to 375:1 (150 ppm MI:0.4 ppm DTBMA vs. *C. albicans*). The results for MBI demonstrate synergy at least for ratios of MI:MBI ranging from 1:6 (10 ppm MI:60 ppm MBI vs. *P. aeruginosa*) to 750:1 (150 ppm MI:0.2 ppm MBI vs. *C. alibanicus*).

Extended Synergy Data

| DTBMA vs. *P. aeruginosa* 9027 in M9GY. MIC at 72 hours | | | | |
|---|---|---|---|---|
| $Q_{MI}$ 25 | | | $Q_{DTBMA}$ 1000 | |
| $Q_{mi}$ | $Q_{dtbma}$ | SI | wt. % MI | wt. % DTBMA |
| 0 | 1000 | 1.00 | 0 | 100 |
| 15 | 300 | 0.90 | 4.76 | 95.24 |
| 20 | 60 | 0.86 | 25.00 | 75.00 |
| 20 | 80 | 0.88 | 20.00 | 80.00 |
| 20 | 100 | 0.90 | 16.67 | 83.33 |
| 25 | 0 | 1.00 | 100 | 0 |

| DTBMA vs. *S. aureus* 6538 in M9GY. MIC at 24 hours | | | | |
|---|---|---|---|---|
| $Q_{MI}$ 60 | | | $Q_{DTBMA}$ 40 | |
| $Q_{mi}$ | $Q_{dtbma}$ | SI | wt % MI | wt % DTBMA |
| 0 | 40 | 1.00 | 0 | 100 |
| 10 | 5 | 0.29 | 66.67 | 33.33 |
| 10 | 6 | 0.32 | 62.50 | 37.50 |
| 10 | 8 | 0.37 | 55.56 | 44.44 |
| 10 | 10 | 0.42 | 50.00 | 50.00 |
| 10 | 20 | 0.67 | 33.33 | 66.67 |
| 10 | 30 | 0.92 | 25.00 | 75.00 |
| 15 | 4 | 0.35 | 78.95 | 21.05 |
| 15 | 5 | 0.38 | 75.00 | 25.00 |
| 15 | 6 | 0.40 | 71.43 | 28.57 |
| 15 | 8 | 0.45 | 65.22 | 34.78 |
| 15 | 10 | 0.50 | 60.00 | 40.00 |
| 15 | 20 | 0.75 | 42.86 | 57.14 |
| 20 | 3 | 0.41 | 86.96 | 13.04 |
| 20 | 4 | 0.43 | 83.33 | 16.67 |
| 20 | 5 | 0.46 | 80.00 | 20.00 |
| 20 | 6 | 0.48 | 76.92 | 23.08 |
| 20 | 8 | 0.53 | 71.43 | 28.57 |
| 20 | 10 | 0.58 | 66.67 | 33.33 |
| 20 | 20 | 0.83 | 50.00 | 50.00 |
| 25 | 2 | 0.47 | 92.59 | 7.41 |
| 25 | 3 | 0.49 | 89.29 | 10.71 |
| 25 | 4 | 0.52 | 86.21 | 13.79 |
| 25 | 5 | 0.54 | 83.33 | 16.67 |
| 25 | 6 | 0.57 | 80.65 | 19.35 |
| 25 | 8 | 0.62 | 75.76 | 24.24 |
| 25 | 10 | 0.67 | 71.43 | 28.57 |
| 25 | 20 | 0.92 | 55.56 | 44.44 |
| 30 | 2 | 0.55 | 93.75 | 6.25 |
| 30 | 3 | 0.58 | 90.91 | 9.09 |
| 30 | 4 | 0.60 | 88.24 | 11.76 |
| 30 | 5 | 0.63 | 85.71 | 14.29 |
| 30 | 6 | 0.65 | 83.33 | 16.67 |
| 30 | 8 | 0.70 | 78.95 | 21.05 |
| 30 | 10 | 0.75 | 75.00 | 25.00 |
| 35 | 2 | 0.63 | 94.59 | 5.41 |
| 35 | 3 | 0.66 | 92.11 | 7.89 |
| 35 | 4 | 0.68 | 89.74 | 10.26 |
| 35 | 5 | 0.71 | 87.50 | 12.50 |
| 35 | 6 | 0.73 | 85.37 | 14.63 |
| 35 | 8 | 0.78 | 81.40 | 18.60 |
| 35 | 10 | 0.83 | 77.78 | 22.22 |
| 40 | 2 | 0.72 | 95.24 | 4.76 |
| 40 | 3 | 0.74 | 93.02 | 6.98 |
| 40 | 4 | 0.77 | 90.91 | 9.09 |
| 40 | 5 | 0.79 | 88.89 | 11.11 |
| 40 | 6 | 0.82 | 86.96 | 13.04 |
| 40 | 8 | 0.87 | 83.33 | 16.67 |
| 40 | 10 | 0.92 | 80.00 | 20.00 |
| 45 | 0.8 | 0.77 | 98.25 | 1.75 |
| 45 | 1 | 0.78 | 97.83 | 2.17 |
| 45 | 2 | 0.80 | 95.74 | 4.26 |
| 45 | 3 | 0.83 | 93.75 | 6.25 |
| 45 | 4 | 0.85 | 91.84 | 8.16 |
| 45 | 5 | 0.88 | 90.00 | 10.00 |
| 45 | 6 | 0.90 | 88.24 | 11.76 |
| 45 | 8 | 0.95 | 84.91 | 15.09 |
| 50 | 0.4 | 0.84 | 99.21 | 0.79 |
| 50 | 0.5 | 0.85 | 99.01 | 0.99 |
| 50 | 0.6 | 0.85 | 98.81 | 1.19 |
| 50 | 0.8 | 0.85 | 98.43 | 1.57 |
| 50 | 1 | 0.86 | 98.04 | 1.96 |
| 50 | 2 | 0.88 | 96.15 | 3.85 |
| 50 | 3 | 0.91 | 94.34 | 5.66 |
| 50 | 4 | 0.93 | 92.59 | 7.41 |
| 50 | 5 | 0.96 | 90.91 | 9.09 |
| 50 | 6 | 0.98 | 89.29 | 10.71 |
| 60 | 0 | 1.00 | 100 | 0 |

| DTBMA vs. *C. albicans* 10231 in PDB. MIC at 48 hours | | | | |
|---|---|---|---|---|
| $Q_{MI}$ 175 | | | $Q_{DTBMA}$ 40 | |
| $Q_{mi}$ | $Q_{dtbma}$ | SI | wt % MI | wt % DTBMA |
| 0 | 40 | 1.00 | 0 | 100 |
| 50 | 2 | 0.34 | 96.15 | 3.85 |
| 50 | 3 | 0.36 | 94.34 | 5.66 |
| 50 | 4 | 0.39 | 92.59 | 7.41 |
| 50 | 5 | 0.41 | 90.91 | 9.09 |
| 50 | 6 | 0.44 | 89.29 | 10.71 |
| 50 | 8 | 0.49 | 86.21 | 13.79 |
| 50 | 10 | 0.54 | 83.33 | 16.67 |
| 50 | 20 | 0.79 | 71.43 | 28.57 |
| 75 | 2 | 0.48 | 97.40 | 2.60 |
| 75 | 3 | 0.50 | 96.15 | 3.85 |
| 75 | 4 | 0.53 | 94.94 | 5.06 |
| 75 | 5 | 0.55 | 93.75 | 6.25 |
| 75 | 6 | 0.58 | 92.59 | 7.41 |
| 75 | 8 | 0.63 | 90.36 | 9.64 |
| 75 | 10 | 0.68 | 88.24 | 11.76 |
| 75 | 20 | 0.93 | 78.95 | 21.05 |
| 100 | 1 | 0.60 | 99.01 | 0.99 |

-continued

DTBMA vs. *C. albicans* 10231 in PDB. MIC at 48 hours

| | | | | |
|---|---|---|---|---|
| 100 | 2 | 0.62 | 98.04 | 1.96 |
| 100 | 3 | 0.65 | 97.09 | 2.91 |
| 100 | 4 | 0.67 | 96.15 | 3.85 |
| 100 | 5 | 0.70 | 95.24 | 4.76 |
| 100 | 6 | 0.72 | 94.34 | 5.66 |
| 100 | 8 | 0.77 | 92.59 | 7.41 |
| 100 | 10 | 0.82 | 90.91 | 9.09 |
| 125 | 0.8 | 0.73 | 99.36 | 0.64 |
| 125 | 1 | 0.74 | 99.21 | 0.79 |
| 125 | 2 | 0.76 | 98.43 | 1.57 |
| 125 | 3 | 0.79 | 97.66 | 2.34 |
| 125 | 4 | 0.81 | 96.90 | 3.10 |
| 125 | 5 | 0.84 | 96.15 | 3.85 |
| 125 | 6 | 0.86 | 95.42 | 4.58 |
| 125 | 8 | 0.91 | 93.98 | 6.02 |
| 125 | 10 | 0.96 | 92.59 | 7.41 |
| 150 | 0.4 | 0.87 | 99.73 | 0.27 |
| 150 | 0.5 | 0.87 | 99.67 | 0.33 |
| 150 | 0.6 | 0.87 | 99.60 | 0.40 |
| 150 | 0.8 | 0.88 | 99.47 | 0.53 |
| 150 | 1 | 0.88 | 99.34 | 0.66 |
| 150 | 2 | 0.91 | 98.68 | 1.32 |
| 150 | 3 | 0.93 | 98.04 | 1.96 |
| 150 | 4 | 0.96 | 97.40 | 2.60 |
| 150 | 5 | 0.98 | 96.77 | 3.23 |
| 175 | 0 | 1.00 | 100 | 0 |

DTBMA vs. *A. niger* 16404 in PDB. MIC at 72 hours

| $Q_{MI}$ 400 | | | $Q_{DTBMA}$ 1500 | |
|---|---|---|---|---|
| $Q_{mi}$ | $Q_{dtbma}$ | SI | wt % MI | wt % DTBMA |
| 0 | 1500 | 1.00 | 0 | 100 |
| 100 | 100 | 0.32 | 50.00 | 50.00 |
| 100 | 200 | 0.38 | 33.33 | 66.67 |
| 100 | 300 | 0.45 | 25.00 | 75.00 |
| 100 | 400 | 0.52 | 20.00 | 80.00 |
| 100 | 500 | 0.58 | 16.67 | 83.33 |
| 100 | 600 | 0.65 | 14.29 | 85.71 |
| 100 | 800 | 0.78 | 11.11 | 88.89 |
| 100 | 1000 | 0.92 | 9.09 | 90.91 |
| 150 | 80 | 0.43 | 65.22 | 34.78 |
| 150 | 100 | 0.44 | 60.00 | 40.00 |
| 150 | 200 | 0.51 | 42.86 | 57.14 |
| 150 | 300 | 0.58 | 33.33 | 66.67 |
| 150 | 400 | 0.64 | 27.27 | 72.73 |
| 150 | 500 | 0.71 | 23.08 | 76.92 |
| 150 | 600 | 0.78 | 20.00 | 80.00 |
| 150 | 800 | 0.91 | 15.79 | 84.21 |
| 200 | 8 | 0.51 | 96.15 | 3.85 |
| 200 | 10 | 0.51 | 95.24 | 4.76 |
| 200 | 20 | 0.51 | 90.91 | 9.09 |
| 200 | 30 | 0.52 | 86.96 | 13.04 |
| 200 | 40 | 0.53 | 83.33 | 16.67 |
| 200 | 50 | 0.53 | 80.00 | 20.00 |
| 200 | 60 | 0.54 | 76.92 | 23.08 |
| 200 | 80 | 0.55 | 71.43 | 28.57 |
| 200 | 100 | 0.57 | 66.67 | 33.33 |
| 200 | 200 | 0.63 | 50.00 | 50.00 |
| 200 | 300 | 0.70 | 40.00 | 60.00 |
| 200 | 400 | 0.77 | 33.33 | 66.67 |
| 200 | 500 | 0.83 | 28.57 | 71.43 |
| 200 | 600 | 0.90 | 25.00 | 75.00 |
| 250 | 3 | 0.63 | 98.81 | 1.19 |
| 250 | 4 | 0.63 | 98.43 | 1.57 |
| 250 | 5 | 0.63 | 98.04 | 1.96 |
| 250 | 6 | 0.63 | 97.66 | 2.34 |
| 250 | 8 | 0.63 | 96.90 | 3.10 |
| 250 | 10 | 0.63 | 96.15 | 3.85 |
| 250 | 20 | 0.64 | 92.59 | 7.41 |

-continued

DTBMA vs. *A. niger* 16404 in PDB. MIC at 72 hours

| | | | | |
|---|---|---|---|---|
| 250 | 30 | 0.65 | 89.29 | 10.71 |
| 250 | 40 | 0.65 | 86.21 | 13.79 |
| 250 | 50 | 0.66 | 83.33 | 16.67 |
| 250 | 60 | 0.67 | 80.65 | 19.35 |
| 250 | 80 | 0.68 | 75.76 | 24.24 |
| 250 | 100 | 0.69 | 71.43 | 28.57 |
| 250 | 200 | 0.76 | 55.56 | 44.44 |
| 250 | 300 | 0.83 | 45.45 | 54.55 |
| 250 | 400 | 0.89 | 38.46 | 61.54 |
| 250 | 500 | 0.96 | 33.33 | 66.67 |
| 300 | 3 | 0.75 | 99.01 | 0.99 |
| 300 | 4 | 0.75 | 98.68 | 1.32 |
| 300 | 5 | 0.75 | 98.36 | 1.64 |
| 300 | 6 | 0.75 | 98.04 | 1.96 |
| 300 | 8 | 0.76 | 97.40 | 2.60 |
| 300 | 10 | 0.76 | 96.77 | 3.23 |
| 300 | 20 | 0.76 | 93.75 | 6.25 |
| 300 | 30 | 0.77 | 90.91 | 9.09 |
| 300 | 40 | 0.78 | 88.24 | 11.76 |
| 300 | 50 | 0.78 | 85.71 | 14.29 |
| 300 | 60 | 0.79 | 83.33 | 16.67 |
| 300 | 80 | 0.80 | 78.95 | 21.05 |
| 300 | 100 | 0.82 | 75.00 | 25.00 |
| 300 | 200 | 0.88 | 60.00 | 40.00 |
| 300 | 300 | 0.95 | 50.00 | 50.00 |
| 400 | 0 | 1.00 | 100 | 0 |

MBI vs. *P. aeruginosa* 9027 in M9GY. MIC at 72 hours

| $Q_{MI}$ 25 | | | $Q_{MBI}$ 200 | |
|---|---|---|---|---|
| $Q_{mi}$ | $Q_{mbi}$ | SI | wt % MI | wt % MBI |
| 0 | 200 | 1.00 | 0 | 100 |
| 15 | 30 | 0.75 | 33.33 | 66.67 |
| 15 | 40 | 0.80 | 27.27 | 72.73 |
| 15 | 50 | 0.85 | 23.08 | 76.92 |
| 15 | 60 | 0.90 | 20.00 | 80.00 |
| 20 | 20 | 0.90 | 50.00 | 50.00 |
| 20 | 30 | 0.95 | 40.00 | 60.00 |
| 20 | 40 | 1.00 | 33.33 | 66.67 |
| 25 | 0 | 1.00 | 100 | 0 |

MBI vs. *S. aureus* 6538 in M9GY. MIC at 24 hours

| $Q_{MI}$ 60 | | | $Q_{MBI}$ 8 | |
|---|---|---|---|---|
| $Q_{mi}$ | $Q_{mbi}$ | SI | wt % MI | wt % MBI |
| 0 | 40 | 5.00 | 0 | 100 |
| 10 | 4 | 0.67 | 71.43 | 28.57 |
| 10 | 5 | 0.79 | 66.67 | 33.33 |
| 10 | 6 | 0.92 | 62.50 | 37.50 |
| 15 | 3 | 0.63 | 83.33 | 16.67 |
| 15 | 4 | 0.75 | 78.95 | 21.05 |
| 15 | 5 | 0.88 | 75.00 | 25.00 |
| 20 | 4 | 0.83 | 83.33 | 16.67 |
| 20 | 5 | 0.96 | 80.00 | 20.00 |
| 25 | 3 | 0.79 | 89.29 | 10.71 |
| 25 | 4 | 0.92 | 86.21 | 13.79 |
| 30 | 2 | 0.75 | 93.75 | 6.25 |
| 30 | 3 | 0.88 | 90.91 | 9.09 |
| 35 | 2 | 0.83 | 94.59 | 5.41 |
| 35 | 3 | 0.96 | 92.11 | 7.89 |
| 40 | 2 | 0.92 | 95.24 | 4.76 |
| 45 | 0.8 | 0.85 | 98.25 | 1.75 |

-continued

MBI vs. *S. aureus* 6538 in M9GY. MIC at 24 hours

| | | | | |
|---|---|---|---|---|
| 45 | 1 | 0.88 | 97.83 | 2.17 |
| 50 | 0.4 | 0.88 | 99.21 | 0.79 |
| 50 | 0.5 | 0.90 | 99.01 | 0.99 |
| 50 | 0.6 | 0.91 | 98.81 | 1.19 |
| 50 | 0.8 | 0.93 | 98.43 | 1.57 |
| 50 | 1 | 0.96 | 98.04 | 1.96 |
| 60 | 0 | 1.00 | 100 | 0 |

MBI vs. *C. albicans* 10231 in PDB. MIC at 48 hours

| $Q_{MI}$ 175 | | | $Q_{MBI}$ 8 | |
|---|---|---|---|---|
| $Q_{mi}$ | $Q_{mbi}$ | SI | wt % MI | wt % MBI |
| 0 | 8 | 1.00 | 0 | 100 |
| 50 | 1 | 0.41 | 98.04 | 1.96 |
| 50 | 2 | 0.54 | 96.15 | 3.85 |
| 50 | 3 | 0.66 | 94.34 | 5.66 |
| 50 | 4 | 0.79 | 92.59 | 7.41 |
| 50 | 5 | 0.91 | 90.91 | 9.09 |
| 75 | 0.8 | 0.53 | 98.94 | 1.06 |
| 75 | 1 | 0.55 | 98.68 | 1.32 |
| 75 | 2 | 0.68 | 97.40 | 2.60 |
| 75 | 3 | 0.80 | 96.15 | 3.85 |
| 75 | 4 | 0.93 | 94.94 | 5.06 |
| 100 | 0.8 | 0.67 | 99.21 | 0.79 |
| 100 | 1 | 0.70 | 99.01 | 0.99 |
| 100 | 2 | 0.82 | 98.04 | 1.96 |
| 100 | 3 | 0.95 | 97.09 | 2.91 |
| 125 | 0.4 | 0.76 | 99.68 | 0.32 |
| 125 | 0.5 | 0.78 | 99.60 | 0.40 |
| 125 | 0.6 | 0.79 | 99.52 | 0.48 |
| 125 | 0.8 | 0.81 | 99.36 | 0.64 |
| 125 | 1 | 0.84 | 99.21 | 0.79 |
| 125 | 2 | 0.96 | 98.43 | 1.57 |
| 150 | 0.2 | 0.88 | 99.87 | 0.13 |
| 150 | 0.3 | 0.89 | 99.80 | 0.20 |
| 150 | 0.4 | 0.91 | 99.73 | 0.27 |
| 150 | 0.5 | 0.92 | 99.67 | 0.33 |
| 150 | 0.6 | 0.93 | 99.60 | 0.40 |
| 150 | 0.8 | 0.96 | 99.47 | 0.53 |
| 150 | 1 | 0.98 | 99.34 | 0.66 |
| 175 | 0 | 1.00 | 100 | 0 |

MBI vs. *A. niger* 16404 in PDB. MIC at 72 hours

| $Q_{MI}$ 400 | | | $Q_{MBI}$ 60 | |
|---|---|---|---|---|
| $Q_{mi}$ | $Q_{mbi}$ | SI | wt % MI | wt % MBI |
| 0 | 60 | 1.00 | 0 | 100 |
| 100 | 10 | 0.42 | 90.91 | 9.09 |
| 100 | 20 | 0.58 | 83.33 | 16.67 |
| 100 | 30 | 0.75 | 76.92 | 23.08 |
| 100 | 40 | 0.92 | 71.43 | 28.57 |
| 150 | 8 | 0.51 | 94.94 | 5.06 |
| 150 | 10 | 0.54 | 93.75 | 6.25 |
| 150 | 20 | 0.71 | 88.24 | 11.76 |
| 150 | 30 | 0.88 | 83.33 | 16.67 |
| 200 | 4 | 0.57 | 98.04 | 1.96 |
| 200 | 5 | 0.58 | 97.56 | 2.44 |
| 200 | 6 | 0.60 | 97.09 | 2.91 |
| 200 | 8 | 0.63 | 96.15 | 3.85 |
| 200 | 10 | 0.67 | 95.24 | 4.76 |
| 200 | 20 | 0.83 | 90.91 | 9.09 |
| 250 | 2 | 0.66 | 99.21 | 0.79 |

-continued

MBI vs. *A. niger* 16404 in PDB. MIC at 72 hours

| | | | | |
|---|---|---|---|---|
| 250 | 3 | 0.68 | 98.81 | 1.19 |
| 250 | 4 | 0.69 | 98.43 | 1.57 |
| 250 | 5 | 0.71 | 98.04 | 1.96 |
| 250 | 6 | 0.73 | 97.66 | 2.34 |
| 250 | 8 | 0.76 | 96.90 | 3.10 |
| 250 | 10 | 0.79 | 96.15 | 3.85 |
| 250 | 20 | 0.96 | 92.59 | 7.41 |
| 300 | 2 | 0.78 | 99.34 | 0.66 |
| 300 | 3 | 0.80 | 99.01 | 0.99 |
| 300 | 4 | 0.82 | 98.68 | 1.32 |
| 300 | 5 | 0.83 | 98.36 | 1.64 |
| 300 | 6 | 0.85 | 98.04 | 1.96 |
| 300 | 8 | 0.88 | 97.40 | 2.60 |
| 300 | 10 | 0.92 | 96.77 | 3.23 |
| 400 | 0 | 1.00 | 100 | 0 |

Testing of Synergistic Combinations in Paint

A paint formulation having a pH of 8.5-8.8 was prepared from an acrylic binder, cellulosic thickener, kaolin, additives for formulation, and water. Fifty grams of the paint samples are inoculated repeatedly with microorganisms isolated from contaminated paint, with rising concentrations of inoculum. This treatment is carried out once a week. Six days after each inoculation, the surviving microorganisms are evaluated in each sample by applying onto nutrient media. These streak-outs are assessed after an incubation time of up to seven days (at 27±2° C. and 85-95% relative atmospheric humidity). An unpreserve sample of the system to be examined is used to check the susceptibility to the growth of microorganisms. Five inoculation cycles are carried out, thus leading to a test duration of six weeks. The rating scale for evaluation microbial growth is as follows:

0=no growth

1=slight growth

2=medium growth

3=heavy growth

The results are presented in the table below.

| ppm active ingredient | | ratio | growth rating |
|---|---|---|---|
| MI | DTBMA | MI:DTBMA | >5 inoc. |
| 0.0 | 0.0 | | 3 |
| 100.0 | 0.0 | 100:0 | 2-3/2 |
| 91.5 | 12.5 | 88:12 | 3 |
| 83.5 | 25.0 | 77:23 | 1-2 |
| 80.0 | 30.0 | 73:27 | 3 |
| 75.0 | 37.5 | 67:33 | 0 |
| 67.0 | 50.0 | 57:43 | 0 |
| 58.5 | 62.5 | 48:52 | 0 |
| 50.5 | 75.0 | 40:60 | 3 |
| 34.0 | 100.0 | 25:75 | 3 |
| 0.0 | 152.0 | 0:100 | 3 |
| 150.0 | 0.0 | 100:0 | 2/1 |
| 137.3 | 18.8 | 88:12 | 1 |
| 125.3 | 37.5 | 77:23 | 2 |
| 120.0 | 45.0 | 73:27 | 3 |
| 112.5 | 56.3 | 67:33 | 0 |
| 100.5 | 75.0 | 57:43 | 0 |
| 87.8 | 93.8 | 48:52 | 0 |
| 75.8 | 112.5 | 40:60 | 0 |
| 51.0 | 150.0 | 25:75 | 3 |
| 0.0 | 228.0 | 0:100 | 3 |

The invention claimed is:

1. A microbicidal composition comprising:
   (a) at least one non-halogenated 2-alkyl-4-isothiazolin-3-one selected from unsubstituted 2-($C_1$-$C_4$)alkyl-4-isothiazolin-3-ones; and
   (b) 2,2'-dithiobis(N-methylbenzamide)
   wherein a weight ratio of said at least one non-halogenated 2-alkyl-4-isothiazolin-3-one to 2,2'-dithiobis(N-methylbenzamide) is from 375:1 to 1:20.

2. The composition of claim 1 in which said at least one non-halogenated 2-alkyl-4-isothiazolin-3-one is 2-methyl-4-isothiazolin-3-one.

3. The composition of claim 2 in which said weight ratio is from 100:1 to 1:20.

4. A paint composition comprising from 50 ppm to 500 ppm of a synergistic microbicide composition; said synergistic microbicide composition comprising:
   (a) 2-methyl-4-isothiazolin-3-one; and
   (b) 2,2'-dithiobis(N-methylbenzamide);
   wherein a weight ratio of 2-methyl-4-isothiazolin-3-one to 2,2'-dithiobis(N-methylbenzamide) is from 375:1 to 1:6.

* * * * *